United States Patent
Ehrlich

(10) Patent No.: US 10,082,486 B2
(45) Date of Patent: Sep. 25, 2018

(54) METHOD FOR RECOGNIZING THE PRESENCE OF LIQUID IN A GAS FLOW

(71) Applicant: SICK Engineering GmbH, Ottendorf-Okrilla (DE)

(72) Inventor: Andreas Ehrlich, Ottendorf-Okrilla (DE)

(73) Assignee: SICK Engineering GmbH, Ottendorf-Okrilla (DE)

( * ) Notice: Subject to any disclaimer, the term of this patent is extended or adjusted under 35 U.S.C. 154(b) by 146 days.

(21) Appl. No.: 15/091,893

(22) Filed: Apr. 6, 2016

(65) Prior Publication Data

US 2016/0305911 A1    Oct. 20, 2016

(30) Foreign Application Priority Data

Apr. 14, 2015    (DE) .................. 10 2015 105 685

(51) Int. Cl.
| | |
|---|---|
| *G01N 29/024* | (2006.01) |
| *G01F 1/66* | (2006.01) |
| *G01F 1/74* | (2006.01) |
| *G01F 1/00* | (2006.01) |

(52) U.S. Cl.
CPC ............. *G01N 29/024* (2013.01); *G01F 1/66* (2013.01); *G01F 1/662* (2013.01); *G01F 1/667* (2013.01); *G01F 1/668* (2013.01); *G01F 1/002* (2013.01); *G01F 1/74* (2013.01)

(58) Field of Classification Search
CPC ......... G01N 29/024; G01F 1/66; G01F 1/661; G01F 1/663; G01F 1/665; G01F 1/666; G01F 1/668; G01F 1/662; G01F 1/667
See application file for complete search history.

(56) References Cited

U.S. PATENT DOCUMENTS

| | | | |
|---|---|---|---|
| 7,886,615 B2 * | 2/2011 | Froehlich ................ | G01F 1/667 73/861.28 |
| 8,155,895 B2 | 4/2012 | Derr et al. | |
| 8,170,812 B2 | 5/2012 | Straub, Jr. | |
| 8,245,582 B2 * | 8/2012 | Lansing ................... | G01F 1/662 73/861.29 |
| 2010/0010756 A1 | 1/2010 | Derr et al. | |
| 2014/0303909 A1 | 10/2014 | Hanks et al. | |

FOREIGN PATENT DOCUMENTS

| | | |
|---|---|---|
| DE | 19717940 A1 | 11/1998 |
| EP | 1186868 A2 | 3/2002 |
| EP | 2428776 B1 | 3/2012 |
| WO | 2013177626 A1 | 12/2013 |

* cited by examiner

*Primary Examiner* — Justin Olamit
(74) *Attorney, Agent, or Firm* — Nath, Goldberg & Meyer; Jerald L. Meyer; Stanley N. Protigal

(57) ABSTRACT

A method for recognizing the presence of liquid (30) in a gas flow flowing in a pipeline uses an ultrasound flowmeter (10). Measurement paths are provided in pairs which are displaced vertically by an equal predefined distance with respect to the center axis such that one lies in an upper region above the center axis and one lies beneath the center axis. A check is made in three stages to define various measurement values, turbulence values and speed of sound values. A liquid warning signal is output when an invalid measurement value is delivered in the first stage, or when the ratio of the turbulence values in the second stage differs from 1 by more than a predefined tolerance value, or when the ratio of the speeds of sound in the third stage differs from 1 by more than a predefined tolerance ratio.

11 Claims, 4 Drawing Sheets

METHOD FOR RECOGNIZING THE PRESENCE OF LIQUID IN A GAS FLOW

Figure 1:
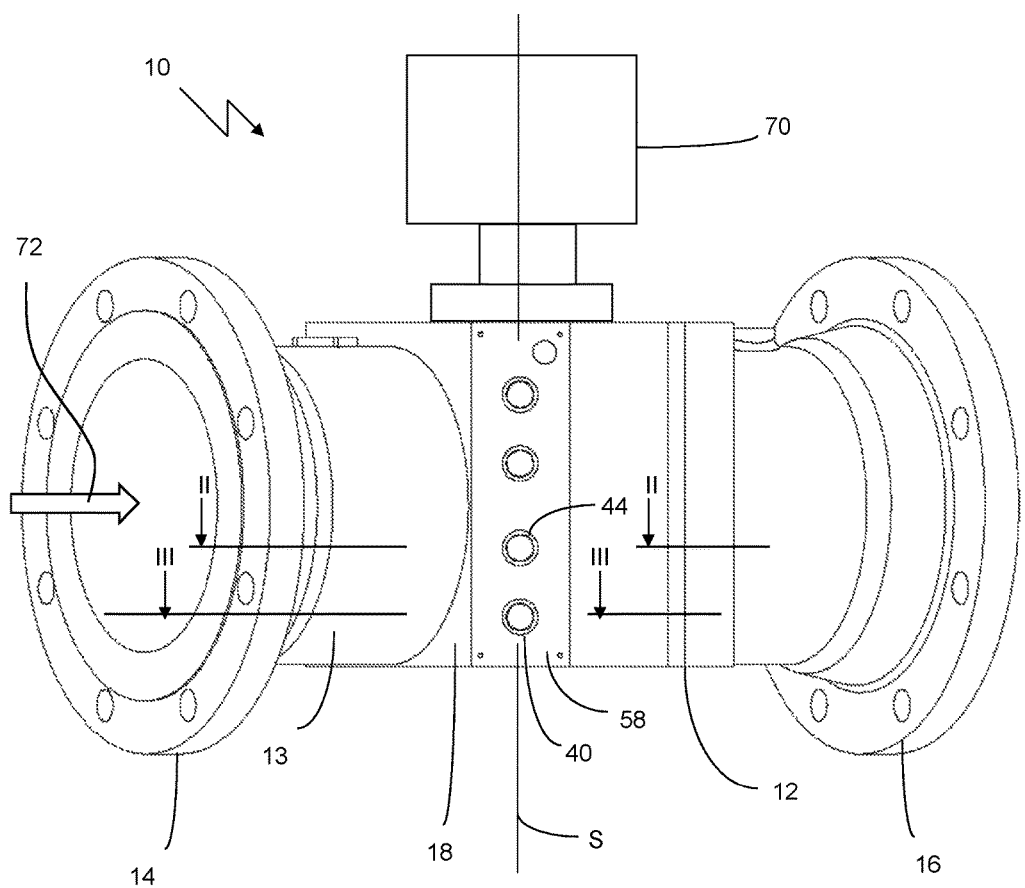

The invention relates to a method for recognizing the presence of liquid in a gas flow flowing in a pipeline and to an ultrasound flowmeter with which this method is carried out.

Different measuring methods and measuring apparatus are known in process flow measurement engineering. Ultrasonic meters are increasingly used for flow measurement. Such a meter is known from EP 2 428 776 B1 and has ultrasonic transducers arranged pairwise, wherein each pair defines a measurement path which lies at a non-perpendicular angle to the longitudinal axis (flow direction) so that the transmitted and received ultrasonic signals propagate along the measurement paths at a specific angle not equal to 90° to the flow direction. The measurement principle comprises a determination of a time of flight difference of two such ultrasonic signals which run in opposite directions on a measurement path and thus have a component in the flow direction, on the one hand, and a component against the flow direction, on the other hand. The flow speed can be calculated from the measured time of flight difference and the flow can be calculated with knowledge of the pipe cross-section.

Very high measurement accuracies are required with such flowmeters which are e.g. used at large natural gas pipelines to determine the gas quantity conducted through since even the smallest differences in the flow measurement can cause large differences in the monetary value with the huge quantities of natural gas.

A factor which contributes to the falsification of a measurement is the presence of liquid in the pipeline. It should thus be recognized at an early time when liquid is present in the measurement zone so that the measurement results can either be evaluated correctly or even corresponding countermeasures can be made.

It is known for this purpose from EP 2 428 776 B1 to determine the flow speeds for the gas on two different, horizontal, parallel planes, with the planes being above and below the center of the pipeline and having the same distance therefrom. In the ideal case and without liquid in the pipe, both flow speeds are the same and also have the same degree of turbulence, with the turbulence in EP 2 428 776 B1 being defined as the statistic variance of the individual values of flow speeds on one plane. If now the respective ratio of the turbulence from the two planes and the ratio of the flow speeds of the gas on the two planes are formed, these ratios are equal to 1 in the ideal case. If deviations from 1 occur, this is as a rule an indication of the presence of liquid since liquid settles at the bottom in the pipeline and therefore influences the lower measurement path more than the further remote upper measurement path. Two indicators are therefore obtained in this manner via which a conclusion can be drawn on the presence of liquid.

Although this solution already delivers good results, it is nevertheless desirable to have even better indicators which are more sensitive and/or respond to further flows.

Starting from this prior art, it is therefore the object of the invention to provide a method and an apparatus with which liquid in the pipeline can be recognized even better and with greater sensitivity.

This object is satisfied by recognizing the presence of liquid in a gas flow flowing in a pipeline using an ultrasound flowmeter having a horizontal pipeline section through which gas can flow in a flow direction and which comprises at least one pair of measurement paths of equal lengths, spaced apart from one another. The pair of measurement paths extend in parallel with one another in separate horizontal planes and are inclined with respect to the flow direction. Each horizontal plane of the measurement paths is displaced vertically by an equal predefined distance with respect to a center axis such that one of the horizontal planes lies in an upper region above the center axis and the other horizontal plane lies in a lower region beneath the center axis. An ultrasonic transducer is arranged at each end of a measurement path, and is configured to act selectively as an ultrasound transmitter and as an ultrasound receiver. Ultrasonic signals can be transmitted and received in both directions on a measurement path and a flow speed of the gas in the plane of the measurement path and the speed of sound in the gas can be determined from the time of flight of the ultrasonic signals, wherein the method is configured in three stages. In a first stage, a check is made whether the bottommost measurement path delivers a valid measurement value for the flow speed of the gas. In a second stage, a turbulence value for each measurement path of a pair of measurement paths is determined from a multiple measurement of the flow speed of the gas in the plane of a measurement path and the ratio of the two turbulence values is formed. In a third stage, the respective speed of sound is determined on both measurement paths of a pair and the ratio of the two speeds of sound is formed. A liquid warning signal is output when an invalid measurement value is delivered in the first stage, when the ratio of the turbulence values differs from 1 by more than a predefined tolerance value in the second stages or when the ratio of the speeds of sound differs from one 1 by more than a predefined tolerance value in the third stage. A check is made before the first step whether the flow speed of the gas exceeds a minimum value and the steps are only carried out when the minimum value is exceeded.

The method in accordance with the invention for recognizing the presence of liquid in a gas flow flowing in a pipeline uses an ultrasound flowmeter. It comprises a horizontal pipeline section through which gas can flow in a flow direction and which has a center axis;

at least one pair of measurement paths of equal lengths which are spaced apart from one another, which extend in parallel with one another in separate horizontal planes and which are inclined with respect to the flow direction;

each horizontal plane of a pair of measurement paths being displaced vertically by an equal, predefined distance with respect to the center axis so that one of the planes lies in an upper region above the center axis and the other plane lies in a lower region beneath the center axis;

an ultrasonic transducer being arranged at each end of a measurement path, with each ultrasonic transducer being configured to act selectively as an ultrasound transmitter and as an ultrasound receiver so that ultrasonic signals can be transmitted and received on one measurement path and the flow speed of the gas in the plane of the measurement path and the speed of sound (SoS) in the gas can be determined on this plane from the measured time of flight of the ultrasonic signals.

The method is formed in three stages in accordance with the invention.

In a first stage, a check is made whether the bottommost measurement path delivers a valid measurement value for the flow speed of the gas.

In a second stage, a turbulence value for each measurement path of a pair is determined from a multiple measurement of the flow speeds of the gas on one measurement path plane and the ratio of the two turbulence values is formed.

In a third stage; the respective speed of sound in the gas is determined on both measurement paths of a pair and the ratio of the two speeds of sound is formed.

A liquid warning signal is output when an invalid measurement value is delivered in the first stage or when the ratio differs from 1 by more than a predefined tolerance value in the second stage or when the ratio of the speeds of sound differs from 1 by more than a predefined tolerance value in the third stage.

A three-stage method has not previously been provided. The gradation has the advantage that a liquid collection can be recognized relatively fast, e.g. as early as in the first stage.

The recognition principle of the second stage is known in principle from EP 2 428 776 B1.

The third stage is new. It would actually be expected that the liquid collections outside a measurement path do not influence the speed of sound in the gas since the speed of sound in the gas is independent of turbulence because it is only a material property.

The inventors have nevertheless surprisingly discovered that liquid collections in the pipe section already influence the speed of sound such that the evaluation in accordance with the invention is possible, even though no liquid collection is present on the measurement path itself. However, fog droplets and other particles whose frequency and/or composition appear(s) to vary with the spacing from the liquid collection are presumably responsible for different speeds of sound in planes having different spacings from the liquid collection. It has been found in this respect that the evaluation in accordance with the invention is even more sensitive and it is thus possible already to recognize liquids in smaller quantities.

The method is configured in three stages and the three stages are advantageously worked through cyclically after one another since each stage has a different sensitivity.

The first stage is the least sensitive, but can be evaluated the fastest. If namely only the bottommost measurement path does not deliver any measurement value for the flow speed of the gas, it is located within the liquid. A further evaluation on the two other stages is then no longer necessary.

The second stage, in which ratios of turbulence are formed, is more sensitive than the determination from the first stage. If liquid is determined in the second stage because the determined ratio differs too much from 1, this is a sign for the presence of liquid and the third stage can be omitted.

Finally, in the third stage, the ratio of the speeds of sound of a pair of measurement paths is determined. It has been found that the ratio of the speeds of sound apparently responds the most sensitively to the presence of liquid in the pipe section. It has at least been found in practice that this ratio responds to cases which are not detected in the first two stages so that this method is used in the last step and smaller quantities of liquid than previously possible can be recognized.

A turbulence value is advantageously defined as a standard deviation over a plurality of measurements of the flow speed of the gas on a measurement path, as is known in principle from EP 2 428 776 B1.

Since the method for recognizing the presence of liquid actually only makes sense when a gas flow is present, provision is made in a further development of the invention that a check is made before the first step whether the flow speed of the gas exceeds a minimum value and the steps for recognizing liquid are only carried out when the minimum value is exceeded. This minimum value can be determined on any one of the measurement paths. The minimum value on the upper plane could preferably be determined since the presence of liquid there is unlikely. It should, however, not be the bottommost measurement path since the likelihood of liquid is the highest there.

The method in accordance with the invention can manage with one pair of measurement paths. If, however, two or more measurement paths are present which then necessarily have to be arranged at different levels, a more accurate sensing of the jet profile can take place. In addition, on a failure of one measurement path, it is possible to move to one or more other pairs of measurement paths.

If a plurality of pairs of measurement paths are present, measurements of different pairs of measurement paths can be made use of in the second and/or third steps. A higher accuracy can result with a suitable linking of the measurements.

From an apparatus aspect, the object is satisfied by an ultrasound flowmeter for measuring the flow of a gas flow through a pipeline. The ultrasound flowmeter comprises:

a horizontal pipeline section through which the gas can flow in a flow direction and which has a center axis;

at least one pair of measurement paths of equal lengths which are spaced apart from one another, which extend in parallel with one another in separate horizontal planes and which are inclined with respect to the flow direction;

each horizontal plane of a pair of measurement paths being displaced vertically by an equal, predefined distance with respect to the center axis so that one of the planes lies in an upper region above the center axis and the other plane lies in a lower region beneath the center axis;

an ultrasonic transducer being arranged at each end of a measurement path, with each ultrasonic transducer being configured to act selectively as an ultrasound transmitter and as an ultrasound receiver so that ultrasonic signals can be transmitted and received on one measurement path and the flow speed of the gas in the plane of the measurement path, on the one hand, and the speed of sound in the gas on the plane of the measurement path, on the other hand, can be determined on the measurement path plane from the measured times of flight of the ultrasonic signals;

a control and evaluation unit, which is configured to carry out the method in accordance with the invention and to recognize the presence of liquid in the pipeline section.

Figure 2:
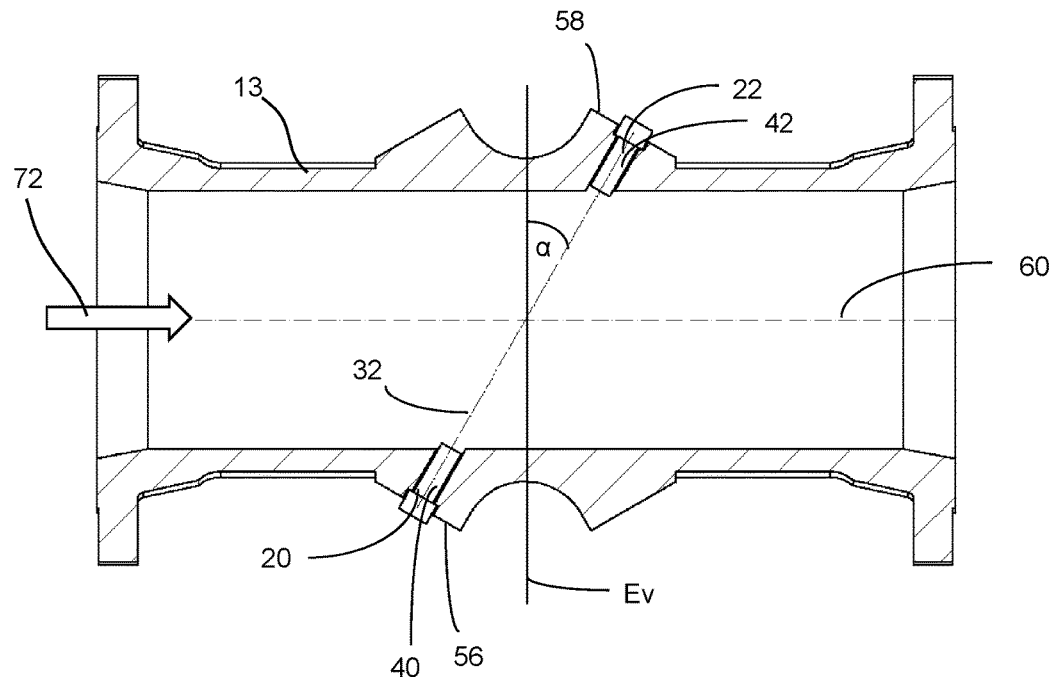
Figure 3:
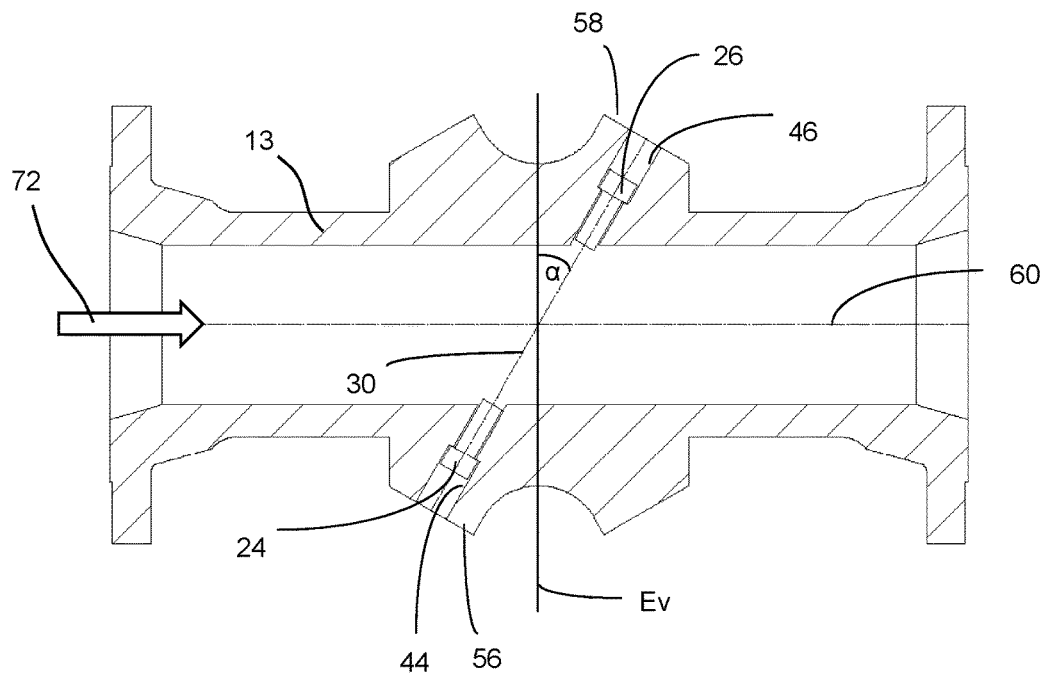
Figure 4:
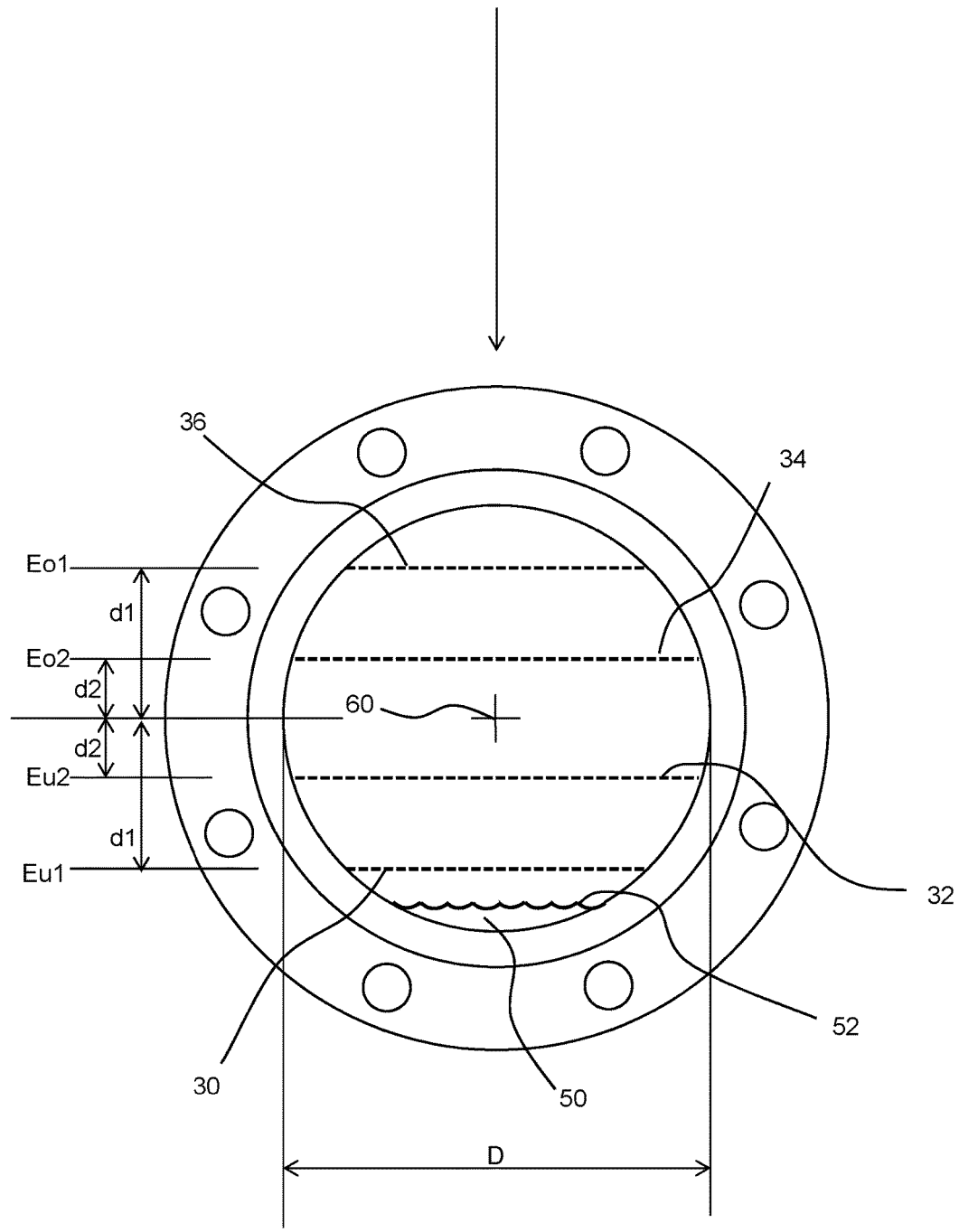

The invention will be explained in detail in the following with reference to an embodiment and to the drawing. There are shown in the drawing:

FIG. 1 a perspective view of an ultrasound flowmeter in accordance with the invention;

FIGS. 2 and 3 cross-sections along the lines II-II and III-III of FIG. 1;

FIG. 4 a view of the ultrasound flowmeter in the longitudinal direction; and

Figure 5:
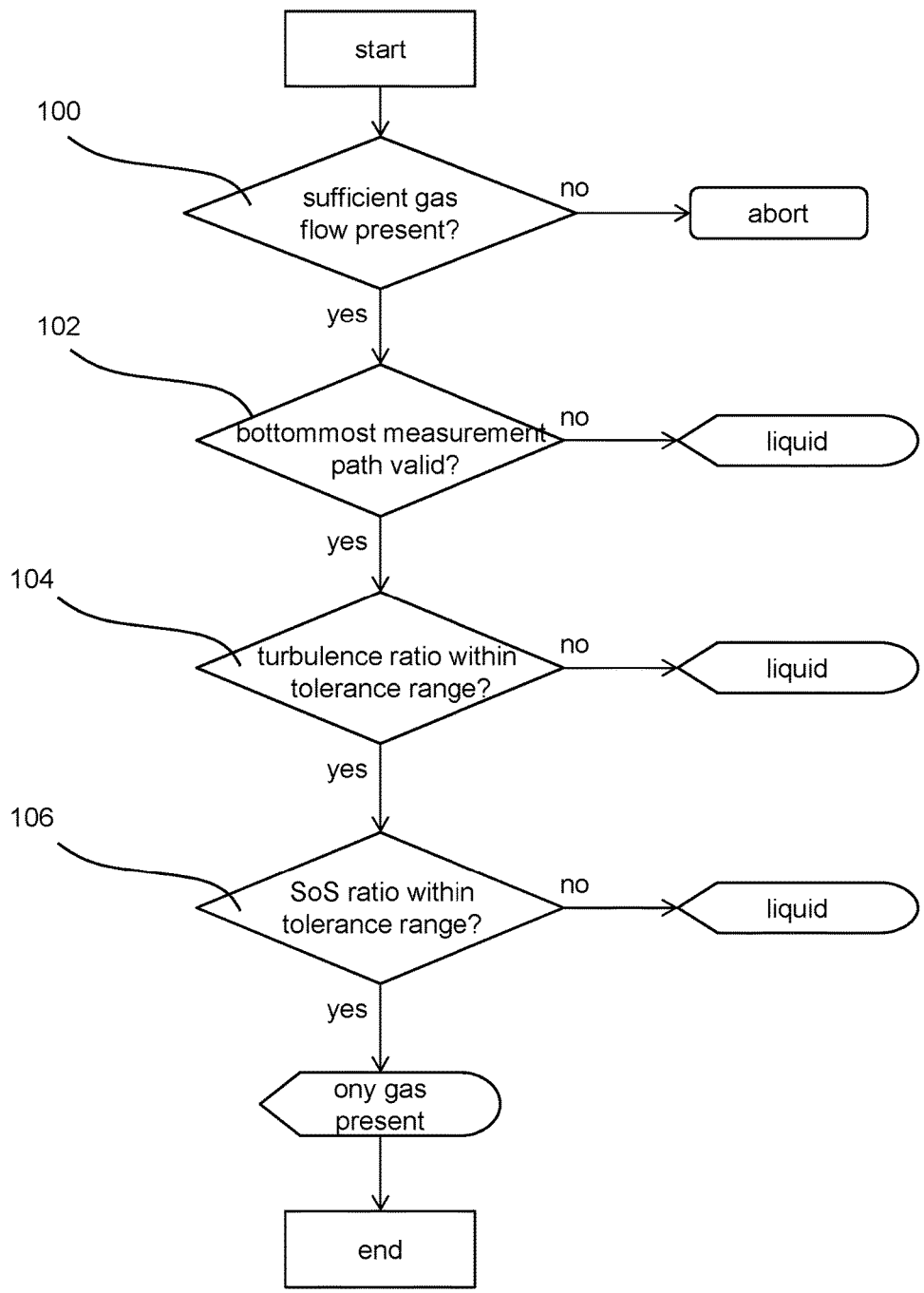

FIG. 5 a flowchart of the method in accordance with the invention.

An apparatus 10 in accordance with the invention has a measurement sensor 12 which comprises a pipeline section 13 arranged between connection flanges 14 and 16. The pipeline section 13 is preferably circular in its interior with a nominal width D corresponding to a pipeline for a gas to be connected to the connection flanges 14 and 16 and not shown in any more detail. The apparatus 10 furthermore has ultrasonic transducers 20, 22, 24, 26 which are respectively arranged pairwise opposite one another in a pipe wall 18, of which only some are shown in the drawing (FIGS. 2 and 3) and which are also simply called probes in the following. The ultrasonic transducers define measurement paths 30, 32, 34, 36, as will be described further below (FIG. 4). For the signal evaluation, the apparatus 10 has a control and evaluation unit 70 which can be fastened to the measurement sensor 12 via a fastening flange. The probes are connectable to the control and evaluation unit 70 via suitable cable connections which are not shown in the drawing. The apparatus in accordance with the invention for measuring the flow speed and/or the flow of a fluid is preferably used as a gas meter.

The probes 20, 22, 24, 26 are held in probe mounts 40, 42, 44, 46 (FIGS. 2 and 3) which are formed as bores in two planar mount surfaces 56 and 58 of the pipe wall 18. The mount surfaces 56 and 58 extend in parallel with one another and are arranged at an angle not equal to 0° to the center axis 60 of the pipeline section 13 which also forms the measurement sensor axis and flow axis (FIGS. 2 and 3).

Respectively oppositely disposed probe mounts 40-42, 44-46 are aligned with one another such that the probes 20, 22, 24, 26 inserted into the probe mounts are aligned with respect to one another and define the measurement paths 30, 32, 34, 36 (FIG. 4). In this respect, the probes transmit and receive ultrasonic signals in a straight line in their longitudinal direction along the respective measurement path 30, 32, 34, 36. All the measurement paths of this embodiment thus run in parallel with one another and are in a common perpendicular plane S (FIG. 4). Each measurement path lies at an angle α to a plane Ev which extends perpendicular to the center axis 60 or to the flow direction 72.

The gas flow flowing through the interior of the measurement sensor 12 is determined in a known manner in that first the flow speed of the gas is determined in that a time of flight difference is measured of ultrasonic signals which run in both directions on a measurement path and thus have a component in and against the flow direction. The flow can be calculated from the flow speed with knowledge of the pipe cross-section. The ultrasonic transducers in this respect serve both as transmitters and as receivers so that each measurement path is used in both directions by the ultrasonic signals.

The speed of sound (SoS) in the gas on the measurement path can be calculated from the time of flight of the ultrasonic signals on a measurement path. The speed of sound SoS is namely the mean value of the speeds of two ultrasonic signals running in opposite directions, that is twice the spacing between the two ultrasonic transducers divided by the sum of the two times of flight there and back.

In the ideal case of an undisturbed, homogeneous, laminar or turbulent flow, one measurement path would be sufficient to determine the flow speed and thus the flow. So that inhomogeneities in the flow profile over the cross-section do not falsify the result, a plurality of measurement paths are provided which sense the flow profile at different points, that is at different spacings from the measurement sensor axis 60. The flow results by suitable integration methods from the individual results for the measurement paths 30, 32, 34, 36. The measurement paths 30, 32, 34, 36 are thus arranged above one another in parallel, horizontal planes Eu1, Eu2, Eo1, Eo2.

The invention now requires a further special arrangement of the measurement paths. Two measurement paths of equal lengths always form a pair of measurement paths. In the embodiment of the drawing, the measurement paths 30 and 36 as well as 32 and 34 each form a pair. The two measurement paths in a pair have equal lengths, extend in parallel with one another and extend in separate horizontal planes Eu1 and Eo1 or Eu2 and Eo2.

Each horizontal plane of a pair is displaced in a vertical direction by an equal predefined distance d1 or d2 respectively with respect to the center axis 60 so that one of the planes Eo1 or Eo2 lies in an upper region above the center axis 60 and the other plane Eu1 and Eu2 lies in a lower region beneath the center axis 60.

The method in accordance with the invention now relates to the recognition of liquid 50 in the pipe section 13. For this purpose, only the measurements are used which are anyway present for the flow determination. The method runs as described in the following and as shown schematically in FIG. 5:

After the start, a check is first made in step 100 whether a sufficient gas flow is present at all since if the flow speed of the gas does not exceed a minimum value, that is if absolutely no flow or too slow a flow is present, the method will not make any sense. It is then also not important whether a liquid 50 is present. This minimum value can be determined theoretically on any one of the measurement paths. The minimum value should preferably be determined on the topmost plane since the presence of liquid there is the most unlikely. At least not the bottommost measurement path should be taken since the likelihood of liquid is the highest there.

In a following step 102 (first stage), a check is made whether the bottommost measurement path 30 delivers a valid measurement value for the flow speed of the gas. If namely there is so much liquid 50 in the pipe section 13 that the liquid level is located above the bottommost plane Eu1, the complete measurement path is in the liquid. A value meaningless for the gas and thus invalid would then be measured for the speed of sound SoS and would make the measurement of a flow speed invalid. If the presence of liquid was determined in this step 102, a liquid warning signal is output. The following steps are then no longer necessary.

In a step 104 (second stage), a turbulence value is determined for each of the two measurement paths of a pair from a multiple measurement of the flow speeds in one direction on a measurement path and the ratio of the two turbulence values is formed. The turbulence value can e.g. be defined by the standard deviation over a plurality of measurements of the flow speed in one direction on a measurement path. If the flow is namely very turbulent, the flow speed will vary more than in a flow which is not so turbulent. A check is then made whether the ratio of the turbulence values differs from 1 by more than a predefinable tolerance value. Without liquid 50 in the pipe section 13, the ratio should be 1 or should be at least very close to 1. If the ratio, however, differs by more than 10%, for example, this can indicate the presence of liquid. It is necessary to determine empirically how large the tolerance values should be. The tolerance values can also differ upwardly and downwardly. They can, for example, be such that the ratio should lie between 0.9 and 1.15. If the presence of liquid was determined in this step 104, a liquid warning signal is output. The following step is then no longer necessary.

Finally, in a third step 106 (third stage), the respective speed of sound SoS is determined on both measurement paths of a pair and the ratio of the two speeds of sound is formed. A check is then made, in an analog manner to the turbulence values, whether the ratio of the speeds of sound differs from 1 by more than a predefined tolerance value.

Numbers are again named as an example. Limits for the ratio can lie at 0.999 and 1.001, for example.

The method in accordance with the invention is preferably carried out permanently and the three stages are worked through cyclically after one another during the operation of the ultrasound flowmeter.

The invention claimed is:

1. A method for recognizing the presence of liquid in a gas flow flowing in a pipeline using an ultrasound flowmeter, wherein the ultrasound flowmeter has a horizontal pipeline section through which gas can flow in a flow direction and which has a center axis and which comprises at least one pair of measurement paths of equal lengths which are spaced apart from one another, with the at least one pair of measurement paths extending in parallel with one another in separate horizontal planes and being inclined with respect to the flow direction; wherein each horizontal plane of a pair of measurement paths is displaced vertically by an equal predefined distance with respect to the center axis such that one of the horizontal planes lies in an upper region above the center axis and the other horizontal plane lies in a lower region beneath the center axis; wherein an ultrasonic transducer is arranged at each end of a respective one of the measurement paths; and wherein each ultrasonic transducer is configured to act selectively as an ultrasound transmitter and as an ultrasound receiver such that ultrasonic signals can be transmitted and received in both directions on a respective one of the measurement paths and a flow speed of the gas in a plane of the measurement path and the speed of sound in the gas can be determined from a time of flight of the ultrasonic signals, wherein the method is configured in three stages, and in a first stage, a check is made whether a bottommost one of the measurement path delivers a valid measurement value for the flow speed of the gas;

in a second stage, a turbulence value for each measurement path of a pair of measurement paths is determined from a multiple measurement of the flow speed of the gas in a plane of a measurement path respective one of the measurement paths and a ratio of the turbulence values for each measurement path is formed;

in a third stage, respective speeds of sound are determined on both measurement paths of a pair and a ratio of the respective speeds of sound is formed;

and a liquid warning signal is output when an invalid measurement value is delivered in the first stage; or when the ratio of the turbulence values for each measurement path differs from 1 by more than a predefined tolerance value in the second stage; or when the ratio of the respective speeds of sound differs from one 1 by more than a predefined tolerance value in the third stage, wherein a check is made before the first stage whether the flow speed of the gas exceeds a minimum value and the three stages are only carried out when the minimum value is exceeded.

2. The method in accordance with claim 1, wherein the three stages are worked through cyclically after one another.

3. The method in accordance with claim 1, wherein a turbulence value is defined as a standard deviation over a plurality of measurements of the flow speeds of the gas on a measurement path plane.

4. The method in accordance with claim 1, wherein the minimum value of the flow speed is not determined on the plane of the bottommost measurement path.

5. The method in accordance with claim 1, wherein a pair of measurement paths is present.

6. The method in accordance with claim 1, wherein two pairs of measurement paths are present.

7. The method in accordance with claim 1, wherein three pairs of measurement paths are present.

8. The method in accordance with claim 1, wherein four pairs of measurement paths are present.

9. The method in accordance with claim 6, wherein measurements of different pairs of the two pairs of measurement paths are made use of in the second and/or third steps.

10. The method in accordance with claim 7, wherein measurements of different pairs of the three pairs of measurement paths are made use of in the second and/or third steps.

11. The method in accordance with claim 8, wherein measurements of different pairs of the four pairs of measurement paths are made use of in the second and/or third steps.

* * * * *